United States Patent [19]

Wojtowicz

[11] 4,024,140

[45] May 17, 1977

[54] PRODUCTION OF ALKALI METAL SALTS OF DICHLOROISOCYANURIC ACID

[75] Inventor: John A. Wojtowicz, Cheshire, Conn.

[73] Assignee: Olin Corporation, New Haven, Conn.

[22] Filed: May 19, 1976

[21] Appl. No.: 687,586

[52] U.S. Cl. .......................................... 260/248 C
[51] Int. Cl.² ..................................... C07D 251/36
[58] Field of Search ............................... 260/248 C

[56] References Cited
UNITED STATES PATENTS 3,896,213  7/1975  Hirdler .......................... 260/248 C
3,988,336  10/1976  Wojtowicz ..................... 260/248 C Primary Examiner—John M. Ford
Attorney, Agent, or Firm—Donald F. Clements; James B. Haglind; Thomas P. O'Day

[57] ABSTRACT

Alkali metal salts of dichloroisocyanuric acid are produced by the reaction of a monoalkali metal cyanurate with hypochlorous acid while maintaining the pH of the reaction mixture in the range of from about 6.0 to about 7.5 and recovering the solid alkali metal dichloroisocyanurates produced thereby.

The products are useful as bleaching or sanitizing agents.

9 Claims, No Drawings

PRODUCTION OF ALKALI METAL SALTS OF DICHLOROISOCYANURIC ACID

This invention relates to a process for the production of alkali metal salts of dichloroisocyanuric acid. The salts are well-known products used in laundry, bleaching, and sanitizing applications.

It is known to produce alkali metal salts of dichloroisocyanuric acid by reacting a dilute solution of trisodium or tripotassium cyanurate with chlorine, as described in U.S. Pat. No. 3,035,056, issued May 15, 1962, to W. F. Symes. This process, however, produces as a by-product large amounts of sodium chloride which contaminate the alkali metal dichloroisocyanurate product and require a multistep procedure for recovering the product from the reaction mixture. In addition, the production of the trialkali metal cyanurate requires superfluous amounts of base, increasing the material costs for the process.

A primary object of the present invention is to provide a process for preparing alkali metal salts of dichloroisocyanuric acid without the formation of contaminating by-products.

Another object of the present invention is to provide an improved process for preparing sodium dichloroisocyanurate.

These and other objects of the invention will be apparent from the following description of the invention.

Briefly, the foregoing objects are accomplished in a process for the production of an alkali metal salt of dichloroisocyanuric acid which comprises reacting a monoalkali metal cyanurate with hypochlorous acid to form a reaction mixture while maintaining the pH of the reaction mixture at from about 6.0 to about 7.5, and recovering the alkali metal salt of dichloroisocyanuric acid.

More in detail, any monoalkali metal cyanurate, such as monosodium, monopotassium, or monolithium cyanurate can be reacted in accordance with the process of this invention. A preferred embodiment is the use of monosodium cyanurate. While the monoalkali metal cyanurate may be reacted as a solid, it is preferred that an aqueous slurry of the monoalkali metal cyanurate be employed as the reactant. For example, the aqueous slurry should be at such a concentration that it can be pumped or conveyed under the reaction conditions employed and yet not be so diluted that an excessive amount of water must be handled. An aqueous slurry of monoalkali metal cyanurate containing from about 10 to about 50 percent, preferably from about 12 to about 35 percent of solids is suitable.

Hypochlorous acid can be made by several widely known methods, including the chlorination of aqueous solutions of alkali metal and alkaline earth metal hypochlorites or carbonates.

In a preferred embodiment, chloride-free hypochlorous acid is used as the hypochlorous acid reagent. It can be prepared by known methods, for example, the reaction of a solution of chlorine in a solvent such as carbon tetrachloride with mercuric oxide produces a solution of chlorine monoxide in the solvent which can be extracted with water to provide an aqueous solution of hypochlorous acid which is free of chloride ions and chlorine (Inorganic Synthesis 5, 158 – 161, 1957).

Hypochlorous acid of any convenient strength can be employed, for example, an aqueous solution containing from about 2 to about 50 percent by weight of HOCl. Preferably, a solution containing from about 10 to about 40 percent is used.

The reaction is believed to proceed according to the following equation in which monosodium cyanurate is used as the monoalkali metal cyanurate:

$$NaH_2C_3N_3O_3 + 2HOCl \rightarrow NaCl_2C_3N_3O_3 + 2H_2O \qquad (1)$$

The feed rates of the monoalkali metal cyanurate and the hypochlorous acid are adjusted to maintain the pH of the reaction mixture at from about 6.0 to about 7.5 and preferably at from about 6.2 to about 7.0.

The reaction is generally carried out using about stoichiometric proportions of reactants. Suitable molar ratios of the monoalkali metal cyanurate to hypochlorous acid range from about 1:1.5 to about 1:2.5, and preferably from about 1:1.8 to about 1:2.2.

During the reaction, the reaction mixture may be maintained at any suitable temperature, for example, at from about 0° to about 50° C, and preferably at from about 10° to about 35° C.

Reaction time is not critical, and any suitable reaction time may be used.

An aqueous slurry or solution of a hydrate of the alkali metal dichloroisocyanurate is produced by this reaction from which the product may be recovered by any suitable means such as filtering, flash drying, or spray graining. When monosodium or monolithium cyanurate are the reactants, sodium dichloroisocyanurate dihydrate and lithium dichloroisocyanurate dihydrate are the reaction products respectively while monopotassium cyanurate produces potassium dichloroisocyanurate monohydrate. Heating the hydrated salt products to the appropriate temperature will form the anhydrous salt or monohydrate, as desired. For example, heating sodium dichloroisocyanurate dihydrate to a temperature in the range of from about 60° to about 90° C forms sodium dichloroisocyanurate monohydrate. Heating the dihydrate to a temperature above about 90° C, preferably in the range of from about 95° C to about 110° C produces anhydrous sodium dichloroisocyanurate.

The novel process of the present invention produces alkali metal dichloroisocyanurates having high available chlorine contents which are free of contaminating salts such as alkali metal chlorides as by-products. Product recovery can be accomplished, for example, by drying the reaction mixture.

The process of the present invention is further illustrated by the following example. All percentages used are by weight unless otherwise specified.

EXAMPLE

A solution of hypochlorous acid which was free of chlorides and chlorine was prepared by passing chlorine gas into a reaction vessel containing 3,200 ml. of $CCl_4$ until the solution contained 160 grams of $Cl_2$. Mercuric oxide, 454 grams, was added to the solution, and the reaction was conducted with agitation at a temperature of about 25° C. After filtering, the $Cl_2O$-containing solution of $CCl_4$ was extracted with water to give a 1.5 molar aqueous solution of hypochlorous acid.

An aqueous slurry of sodium cyanurate monohydrate (0.127 mole) was added to a reaction vessel containing 35 ml. of water. Simultaneously added to the reaction vessel was 0.254 mole of the aqueous hypochlorous acid solution at a rate which maintained the pH of the reaction mixture at about 6.5. The addition of the reagents occurred over a 30-minute period. The reaction product was recovered by evaporating the solution and sodium dichloroisocyanurate dihydrate (0.126 mole) having an available chlorine content of 54 percent was obtained (theoretical chlorine content 55%).

What is claimed is:

1. A process for the production of an alkali metal salt of dichloroisocyanuric acid which comprises reacting a monoalkali metal cyanurate with hypochlorous acid to form a reaction mixture while maintaining the pH of said reaction mixture at from about 6.0 to about 7.5, and recovering said alkali metal salt of dichloroisocyanuric acid.

2. The process of claim 1 in which the temperature of the reaction mixture is maintained at from about 0° to about 50° C.

3. The process of claim 1 wherein the molar ratio of said monoalkali metal cyanurate to said hypochlorous acid is from about 1:1.5 to about 1:2.5.

4. The process of claim 1 in which said monoalkali metal cyanurate is monosodium cyanurate.

5. The process of claim 4 in which said temperature of said reaction mixture is maintained at from about 10° to about 35° C.

6. The process of claim 5 in which said molar ratio of said monosodium cyanurate to said hypochlorous acid is from about 1:1.8 to about 1:2.2.

7. The process of claim 6 in which said pH of said reaction mixture is maintained at from about 6.2 to about 7.0.

8. The process of claim 5 in which an aqueous slurry of said monosodium cyanurate is reacted.

9. The process of claim 8 in which said sodium dichloroisocyanurate produced is sodium dichloroisocyanurate dihydrate.

* * * * *